(12) United States Patent
Kraft et al.

(10) Patent No.: US 10,195,360 B2
(45) Date of Patent: Feb. 5, 2019

(54) MEMBER AND ASSEMBLY FOR A DRUG DELIVERY DEVICE, DRUG DELIVERY DEVICE AND USE OF A MEMBER

(71) Applicant: Sanofi-Aventis Deutschland GMBH, Frankfurt am Main (DE)

(72) Inventors: Torsten Kraft, Frankfurt am Main (DE); Markus Oschmann, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 61 days.

(21) Appl. No.: 15/026,700

(22) PCT Filed: Nov. 10, 2014

(86) PCT No.: PCT/EP2014/074144
§ 371 (c)(1),
(2) Date: Apr. 1, 2016

(87) PCT Pub. No.: WO2015/071210
PCT Pub. Date: May 21, 2015

(65) Prior Publication Data
US 2016/0287806 A1    Oct. 6, 2016

(30) Foreign Application Priority Data

Nov. 15, 2013 (EP) .................................... 13193013

(51) Int. Cl.
*A61M 5/315* (2006.01)

(52) U.S. Cl.
CPC .... *A61M 5/31568* (2013.01); *A61M 5/31551* (2013.01); *A61M 5/31585* (2013.01); *A61M 2205/581* (2013.01); *A61M 2205/582* (2013.01)

(58) Field of Classification Search
CPC ........ A61M 5/31551; A61M 2205/581; A61M 2205/582; A61M 5/31568; A61M 5/31585
See application file for complete search history.

(56) References Cited

U.S. PATENT DOCUMENTS

2008/0306445 A1    12/2008  Burren et al.

FOREIGN PATENT DOCUMENTS

| DE | 102007054019 | 5/2007 |
|----|-------------|--------|
| JP | 2009-507581 | 2/2009 |
| JP | 2013-512070 | 4/2013 |
| JP | 2013-539697 | 10/2013 |
| WO | WO2004/078241 | 9/2004 |
| WO | WO 2005/018721 | 3/2005 |

(Continued)

OTHER PUBLICATIONS

International Search Report and Written Opinion in International Application No. PCT/EP2014/074144, dated Feb. 2, 2015, 13 pages.

(Continued)

*Primary Examiner* — Rebecca E Eisenberg
(74) *Attorney, Agent, or Firm* — Fish & Richardson P.C.

(57) ABSTRACT

A member (1) for a drug delivery device is provided, the member comprising a main body (10), an interaction section (13) and a resilient section (12). Moreover, the main body (1) is unitarily formed with the resilient section (12) and the interaction section (13), wherein the resilient section (1) connects the main body (10) and the interaction section (13), and wherein the interaction section (13) comprises a clicker feature (14).

18 Claims, 5 Drawing Sheets

(56) References Cited

FOREIGN PATENT DOCUMENTS

WO  WO 2011/068531  6/2011
WO  WO 2012/049141  4/2012

OTHER PUBLICATIONS

International Preliminary Report on Patentability in International Application No. PCT/EP2014/074144, dated May 17, 2016, 8 pages.
Rote Liste, "50. Hypophysen-, Hypothalamushormone, andere regulatorische Peptide u. ihre Hemmstoffe," Chapter 50, ed. 2008, 20 pages.

MEMBER AND ASSEMBLY FOR A DRUG DELIVERY DEVICE, DRUG DELIVERY DEVICE AND USE OF A MEMBER

CROSS-REFERENCE TO RELATED APPLICATIONS

This application is a U.S. national stage application under 35 USC § 371 of International Application No. PCT/EP2014/074144, filed on Nov. 10, 2014, which claims priority to European Patent Application No. 13193013.3, filed on Nov. 15, 2013, the entire contents of which are incorporated herein by reference.

The present disclosure relates to a member for a drug delivery device, and an assembly for a drug delivery device, a drug delivery device and the use of a member for a clicker mechanism in a drug delivery device.

Aspects of the invention may include a member and/or an assembly with which a drug delivery device can be improved. Particularly, the drug delivery device can be embodied more robust when the member and/or the assembly is applied to it.

Aspects of the invention may include a member for a drug delivery device, the member comprising a main body, and interaction section and a resilient section. The main body is unitarily formed with the resilient section and the interaction section, wherein the resilient section connects the main body and the interaction section, and wherein the interaction section comprises a clicker feature. The member may be a clicker member. Additionally or alternatively, the member may be a clutch member, e.g. configured to interact with a clutch feature, e.g. of the assembly or the drug delivery device. With the provision of the main body, preferably, a rigid main body, and the resilient section, the member may be configured to adopt a functionality of a rigid, as well as of a resilient component. The interaction section or the clicker feature thereof is, preferably, configured for an interaction with a further component, e.g. a clicker component, such as a counter clicker.

In an embodiment, the main body comprises an additional feature being configured to interact with a clutch feature, e.g. of an assembly or a drug delivery device. According to this embodiment, the member may be a clutch member or at least partly adopt the role of clutch member, e.g. in an assembly or a drug delivery device. Such a clutch member or clutch functionality may be crucial or advantageous for the functioning or the operation of the assembly or the device.

In an embodiment, the member comprises in the resilient section cut-outs to provide the resilience to the resilient section. According to this embodiment, the resilient section can be formed out even though the interaction section, the resilient section and the main body are formed unitarily.

The unitary embodiment, in turn, provides the advantage of robustness, as thereby, a low number of interacting parts of the assembly can be achieved. Due to the formation of cut-outs, webs may be formed out in the resilient section which act as resilient arms of the resilient section.

In an embodiment, the member comprises a sleeve-like shape. As an advantage, the member may be, preferably axially, guided in a housing of the assembly. In this respect, any functionality which relates to the member, can be rendered robust.

In an embodiment, the member comprises two cut-outs which are axially spaced with respect to each other. An axial space between the mentioned cut-outs may, expediently, award the resilience to the resilient section, provided that a solid portion such as a web of the member defining one of the cut-outs can spring or deflect into the respective other one of the mentioned cut-outs.

In an embodiment, the member comprises at least one protrusion protruding into at least one cut-out, the protrusion being arranged to limit the resilient movement of the resilient section. According to this embodiment, a deflection of the resilient movement of the member can, advantageously, be adjusted.

A further aspect relates to an assembly for a drug delivery device comprising the member, a housing and an interaction element. The interaction element may be axially and/or rotationally secured with respect to the housing and the member. Preferably, the interaction element is rotationally secured with respect to the housing such that no relative rotation between these parts is allowed or possible. The assembly is, preferably configured such that the member is rotatable with respect to the interaction element. The housing may comprise a main axis. The main axis may be a longitudinal axis of the housing. The assembly further comprises a clicker mechanism comprising the interaction element and the clicker feature. The assembly is configured such that, during an operation of the clicker mechanism, a relative rotation between the member and the interaction element is performed such that the resilient section is elastically deformed and the clicker feature interacts with the interaction element to perform a clicker action. The provision of the member, as described, allows for providing an assembly with an improved clicker and/or clutch functionality, particularly an assembly which, when applied in a drug delivery device, can be embodied more robust and user-friendly. In particular, malfunctions of spring elements to which the drug delivery devices may be prone, can be prevented. Particularly, a fixation or bearing of a resilient element in the housing can be improved. Such a resilient element may also be important for the mentioned clutch functionality. Moreover the generation of e.g. an audible clicker, particularly during a setting of a dose of drug can easily be achieved. With the provision of the member, the assembly can be embodied such that a pull-out of the resilient element, in case that said element is a single or separate spring element, can be prevented. Such pull-out may be caused by a malfunction or misoperation of a user of the assembly or the device, particularly, when an injection needle of the assembly or device is blocked. Then, components of the assembly or the device may be deformed or distorted. When, for instance, the single spring element is ripped off its bearing in the housing, the assembly or the drug delivery device is not usable anymore.

A further aspect relates to a drug delivery device comprising the assembly.

The clicker feature may comprise or constitute teeth. Accordingly, the interaction element may comprise teeth which match the teeth of the clicker feature.

An operation of the assembly may relate to a dose setting operation, wherein a dose of drug is set or a dose dispensing operation, wherein a previously set dose is dispensed, for instance.

In an embodiment, the assembly is configured such that, the main body is displaceable relative to the clicker feature between a first position and a second position being different from the first position, wherein in the first position, the member is rotatable with respect to the interaction element, and in the second position, a relative rotation of the member and the interaction element is prevented. The first position and the second position may be distinguished by the relative axial arrangement of the main body with respect to the housing. According to this embodiment, a clicker action or functionality of the clicker mechanism may be achieved, wherein a relative rotation between the interaction element and the member is necessary.

In an embodiment, the assembly is configured such that, in the first position of the main body, the clicker feature is displaceable against the resilience of the resilient section and, in the second position of the main body, the clicker feature interacts with the interaction element such that the clicker feature is not displaceable against the resilience of the resilient section. With this embodiment, a clicker functionality can be provided most expediently, as the resilient section of the member can deflect, while being unitarily formed by the main body.

In an embodiment, the clicker feature comprises a toothed surface which extends circumferentially around the member. As an advantage, the clicker mechanism can be embodied robust.

In an embodiment, the clicker mechanism is suitable to provide for an audible and/or tactile feedback to a user when the member is rotated with respect to the housing in the first position of the main body. This, advantageously, enhances usability and safety of the assembly or the drug delivery device.

In an embodiment of the drug delivery device, the drug delivery device comprises a clutch mechanism which comprises the clutch feature and the additional feature which are arranged to engage each other in a clutch engagement (cf. above). Moreover, the drug delivery device is configured such that, the clutch feature and the additional feature are biased into the clutch engagement by the resilient section, and wherein, in the first position of the main body, the clutch engagement is engaged and, in the second position of the main body, the clutch engagement is released. The clutch feature may be provided by a sleeve of the drug delivery device, such as a dial sleeve, for example. By means of the clutch mechanism, relative rotation of the member and the component comprising the clutch feature can, advantageously, selectively be prevented or allowed, e.g. depending on the operational state of the assembly or the drug delivery device. The release of the clutch mechanism may be advantageous, e.g. in a dispensing state of the drug delivery device, wherein a component which is clutchable, such as rotationally lockable, with respect to the member has to be rotatated with respect to the member.

In an embodiment of the drug delivery device, the drug delivery device comprises, in addition to the clutch mechanism, a feedback mechanism which comprises a first feedback feature and a second feedback feature provided by the main body, wherein the feedback mechanism is configured such that a relative rotation of the first and the second feedback feature is converted into a feedback by mechanical cooperation of the first and the second feedback feature. The first feedback feature may also be provided by the above-mentioned sleeve. The feedback mechanism may be a dispense clicker mechanism, i.e. a clicker mechanism operated during a dispensing operation, for example. The feedback mechanism may, as well as the clicker mechanism, provide for an audible and/or tactile feedback to the user.

As a further aspect, a use of a member for a clicker mechanism in a drug delivery device is presented.

The term "drug", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl- ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser -Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39), des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4 (1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4 (1-39)-(Lys)6-NH2,
H-(Lys)6-des Pro36 [Trp(O2)25, Asp28] Exendin-4(1-39)-Lys6-NH2, H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(0)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2) 25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Features which are described herein above and below in conjunction with different aspects or embodiments, may also apply for other aspects and embodiments. Further features and advantageous embodiments of the subject-matter of the disclosure will become apparent from the following description of the exemplary embodiment in conjunction with the figures, in which:

Like elements, elements of the same kind and identically acting elements may be provided with the same reference numerals in the figures. Additionally, the figures may be not true to scale. Rather, certain features may be depicted in an exaggerated fashion for better illustration of important principles.

Figure 1:
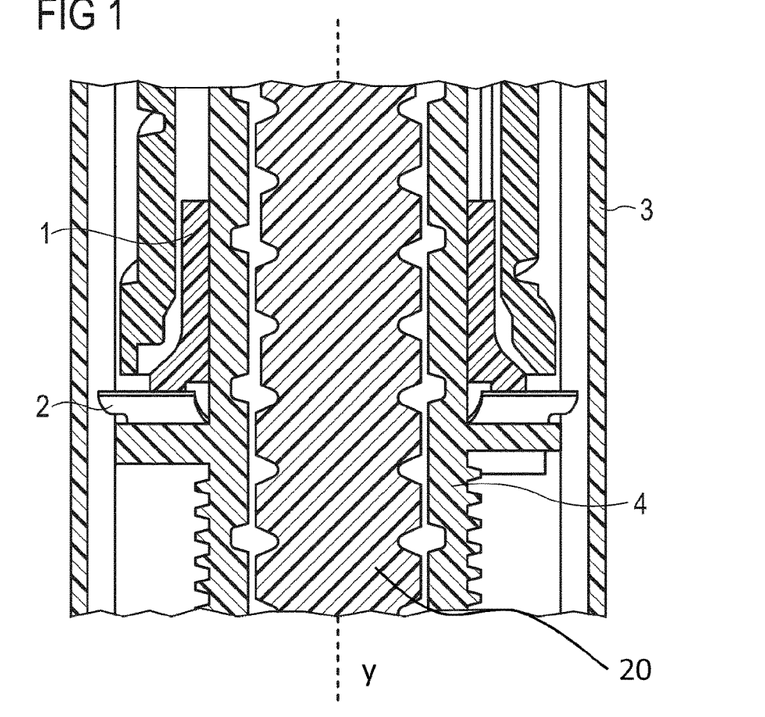
FIG. 1 shows a longitudinal section of a portion of an assembly which is not in accordance with the present disclose.

In FIG. 1 a portion of an assembly is shown, wherein the assembly is not subject of the present disclosure. The assembly comprises a clutch member 1. The clutch member may be a sleeve. The assembly further comprises a spring element 2 which may be a leave spring. The clutch member 1 is arranged above or proximally beside the spring element 2. The assembly further comprises a drive sleeve 4. The drive sleeve 4 extends through the clutch member 1 and the spring element 2. The drive sleeve 4 may be rotationally locked with respect to the clutch member 1. The spring element 2 is shown in a biased or compressed, preferably completely compressed, state.

The assembly further comprises a housing 3 with a longitudinal axis Y. The housing houses the remaining components of the assembly. The assembly further comprises a piston rod 20 which extends through the drive sleeve 4.

Figure 2:
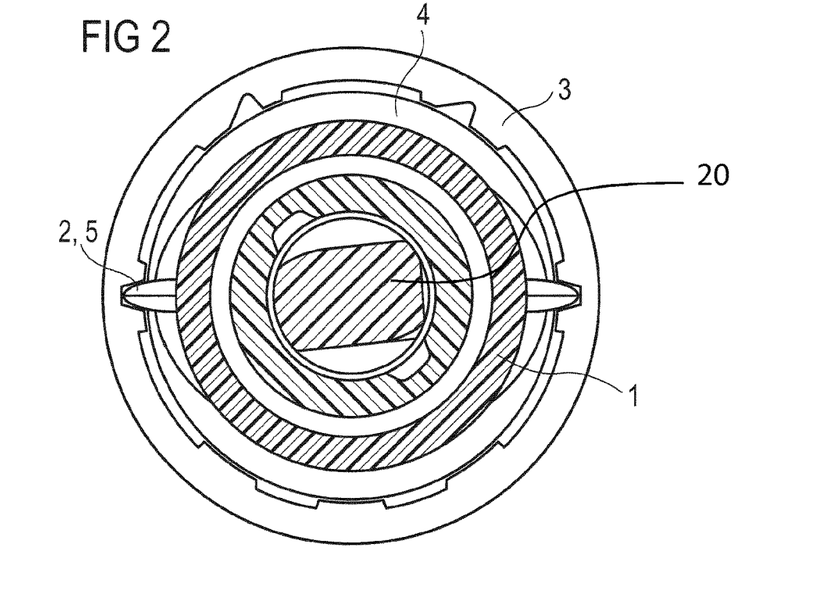
FIG. 2 shows a cross-sectional view of an assembly or a drug delivery device according to the assembly shown in FIG. 1.

FIG. 2 shows a cross-sectional view of the assembly shown in FIG. 1. It is shown that the spring element 2 comprises protrusions 5 which serve the purpose for rotationally locking the spring element 2 with respect to the housing 3.

Figure 3:
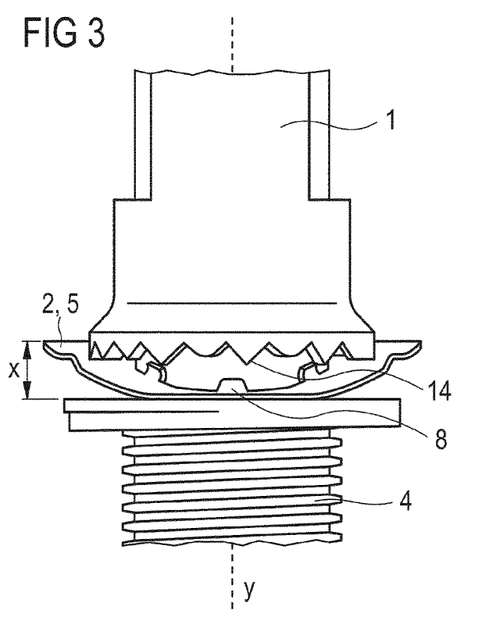
FIG. 3 shows a side-view of parts of the assembly shown in FIGS. 1 and 2.

FIG. 3 shows a side view of parts of the assembly shown in FIGS. 1 and 2. The spring element 2 is shown in a relaxed or partly relaxed state. In the depicted situation, the clutch member 1 is shown in a first (axial) position, e.g. with respect to the housing (not explicitly indicated in FIGS. 3 and 4). It is shown that the clutch member 1 comprises a clicker feature 14 which may comprise a toothed surface. The spring element 2 comprises a counter clicker 8. The counter clicker 8 further comprises teeth. The counter clicker 8 is, preferably, configured to interact with the clicker feature 14 to form a clicker mechanism.

The distance X refers to the axial distance or deflection (if applicable corrected by the axial thickness of the material of the spring element 2) by which the clutch member 1 may be moved axially with respect to the housing or the drive sleeve 4 in order to move the clutch member 1 from a first position to a different, second (axial) position. During said movement, the spring element 2 is compressed.

Figure 4:
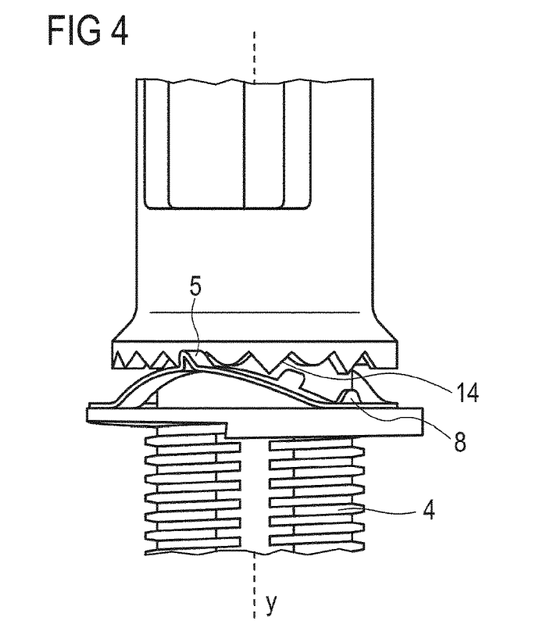
FIG. 4 shows a side-view of parts of the assembly shown in FIG. 3 from a different perspective.

FIG. 4 shows parts of the assembly from a perspective in which the assembly has been rotated around the longitudinal axis Y with respect to FIG. 3.

When the clutch element 1 is rotated with respect to the housing which is not explicitly indicated or with respect to e.g. the drive sleeve 4, the clicker mechanism mentioned above is activated and the spring element 2 is biased when e.g. tooth of the clicker feature 7 passes or moves over a tooth of the counter clicker 8. When the clutch member 1 is rotated relative to the spring element 2, the clicker feature 7 may click over the counter clicker of the spring element 3 such that an audible or tactile feedback is provided to the user. Each click may correspond to a unit dose of a drug.

Such a rotation may relate to a dose setting or dialling operation of the assembly or a corresponding drug delivery device to which the assembly is applied.

Although this is not explicitly indicated, a dose dial sleeve, e.g. of the assembly may be provided outside of the clutch member 1 and radially inward of the housing. The dose dial sleeve may be clutched, such as rotationally locked, to the clutch member 1 when the clutch member 1 is in the first position.

To dial a dose, a user may then rotate a dose dial grip with respect to the housing. The drive sleeve 4, the clutch member 1 and the dose dial sleeve may then rotate together with respect to the housing. The assembly may be configured accordingly.

When the desired dose has been dialed or set, the user may dispense this dose by depressing an activation button (not explicitly indicated), for example. This displaces the clutch member 1 axially with respect to the dose dial sleeve from the first to the second position, wherein the mentioned clutch mechanism is released. Furthermore, by the interaction of the teeth of the clicker feature 14 and the counter clicker 8, the clutch member 1 and with it the drive sleeve are hindered from being rotated with respect to the housing. However, the drive sleeve 4 may be axially moved with respect to the housing and the assembly may be configured such that the longitudinal axial movement of the drive sleeve causes a piston rod of the assembly or the device to rotate, thereby advancing a piston in a cartridge to dispense a dose of drug.

Figure 5:
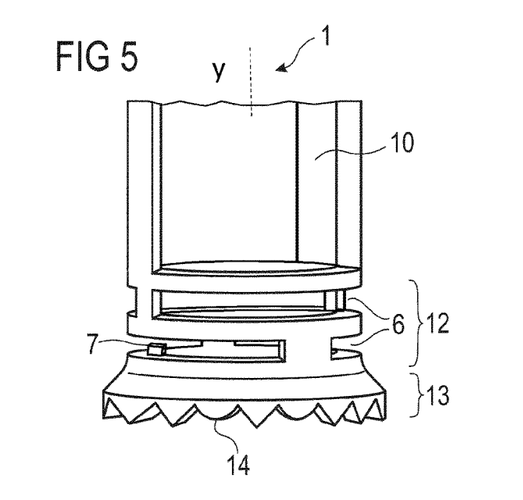
FIG. 5 shows a side-view of a member according to the present disclosure.

FIG. 5 shows at least a part of a member 1 of the assembly according to the present disclosure. The member 1 comprises a main body 10. The member 1 comprises a sleeve-like shape. The member 1 further comprises a resilient section 12. Furthermore, the member 1 comprises an interaction section 13. The resilient section 12 connects the main body 10 and the interaction section 13. The resilient section 12 comprises cut-outs or slots 6. The cut-outs 6 are configured to provide the resilience of the resilient section. The cut-outs 6 are defined by webs (not explicitly indicated). Two cut-outs 6 are depicted which are axially spaced with respect to each other. The resilient section further comprises a protrusion 7 protruding into the distal-most cut-out which is configured to limit the resilient movement of the resilient section.

The "distal end" of the assembly or the drug delivery device or a component thereof shall mean the end which is closest to a dispensing end of the drug delivery device.

The "proximal end" of the assembly or the drug delivery device or a component thereof shall mean the end which is furthest away from the dispensing end of the drug delivery device.

Figure 7:
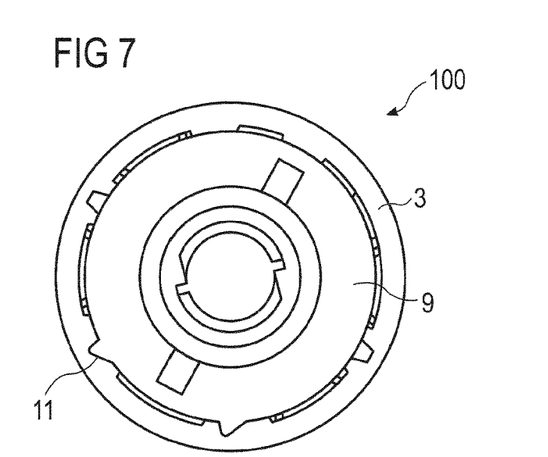
FIG. 7 shows a cross-sectional view of an embodiment of an assembly according to the present disclosure.
Figure 8:
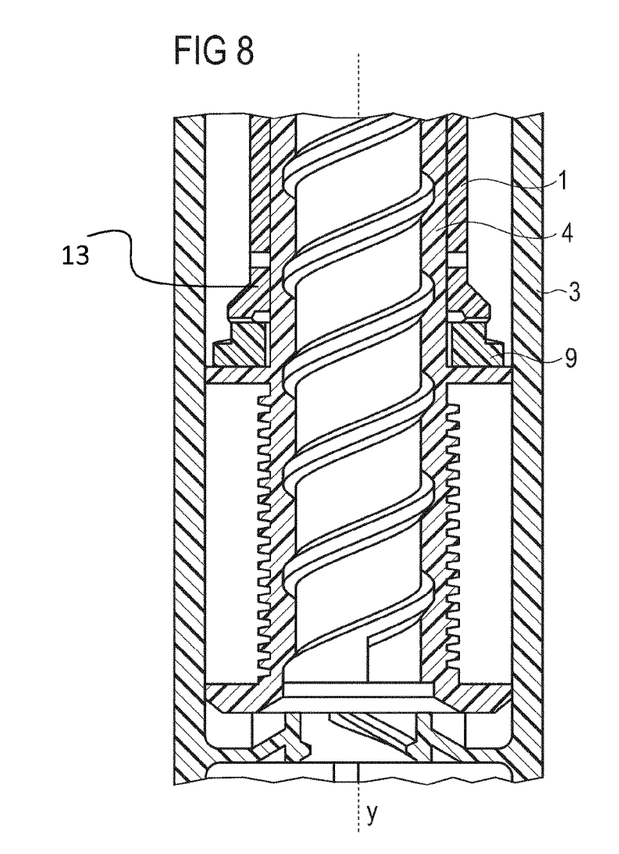
FIG. 8 shows a longitudinal section of an embodiment of the assembly shown in FIG. 7.
Figure 9:
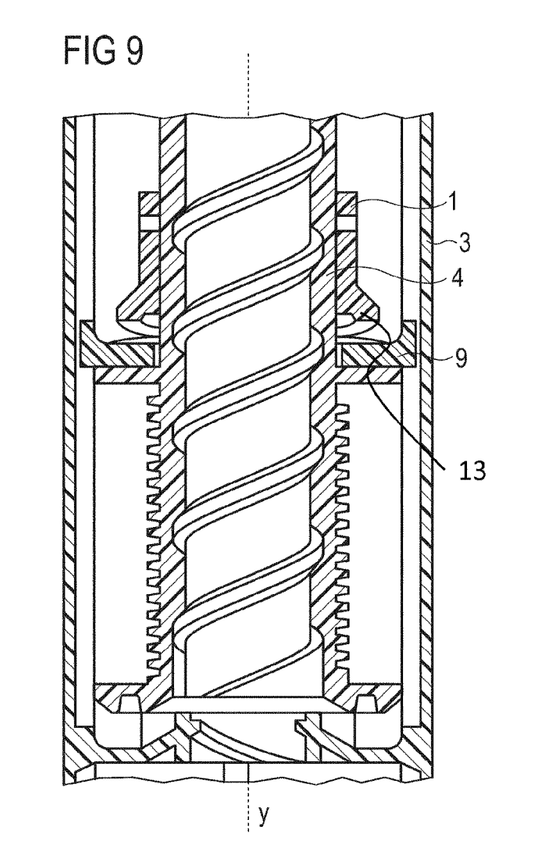
FIG. 9 shows a longitudinal section of the assembly shown in FIG. 8 from a different perspective.

The configuration of the cut-outs and/or the resilient section 12 is, preferably, configured such that the resilience of the resilient section 12 is adjusted to the particular requirement of a clicker mechanism in an assembly 100 (see FIGS. 7 to 9).

The main body 10 of the member 1 is unitarily formed with the resilient section 12 and the interaction section 13. The interaction section 13 further comprises a clicker feature 14. A clicker feature 14 may comprise or constitute a toothed surface or comprises teeth, as mentioned above. Preferably, the toothed surface or teeth of the clicker feature 14 extend circumferentially around the member 1.

Figure 6:
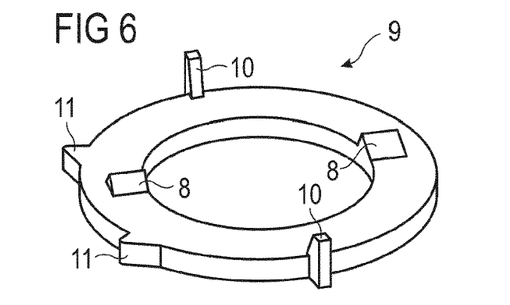
FIG. 6 shows a perspective view of an interaction element according to the present disclosure.

FIG. 6 shows perspective view of an interaction element 9 of the assembly 100. The interaction element 9 comprises a ring-like shape. The interaction element 9 comprises a counter clicker 8 comprising or consisting of teeth. The teeth are further arranged to oppose each other around a circumference of the interaction element 9. The teeth are, expediently, configured to interact with those of the clicker feature 14 of the member 1 to form the clicker mechanism. Expediently, the clicker mechanism is suitable to provide for an audible and/or tactile feedback to a user when the member 1 is rotated with respect to the housing 3 in a first position of the main body 10.

The interaction element 9 further comprises fixation elements 5 which are arranged at an outer circumference of the interaction element 9. The fixation elements 5 are further arranged opposingly. The interaction element 9 further comprises guidance pins 11. FIG. 6 shows two guidance pins 11, each comprising a steep and a flat side face. The guidance pins 11 are provisioned to improve a fixation of the interaction element 9 in or with respect to the housing 3 (cf. FIGS. 7 to 9). Particularly, the guidance pins 11 may prevent a pull-out of the interaction element 9 from the housing 3.

FIG. 7 shows a cross-sectional view of the housing 3 and the interaction element 9 mounted to the housing 3. One can see that the guidance pins 11 and the protrusions 10 fit into corresponding slots or recesses of the housing 3 such that the interaction element 9 is rotationally locked with respect to the housing 3.

FIG. 8 shows a longitudinal section of parts of an assembly 100 according to the present disclosure. In contrast to the assembly shown in FIGS. 1 to 4, a single spring element is not present. Instead the assembly 100 comprises the member 1 which may constitute a clutch member. The assembly further comprises the housing 3 and the described interaction element 9. The assembly further comprises the clicker mechanism comprising the interaction element 9 and the clicker feature 14. The assembly is configured such that, during an operation of the clicker mechanism, a relative rotation between the member 1 and the interaction element 9 is performed such that the resilient section 12 is elastically deformed and the clicker feature 14 interacts with the interaction element 9 to perform a clicker action (cf. above). Thereby, the main body 10 is displaceable relative to the clicker feature 9 between the first position and the second position. In the first position, the member 1 is rotatable with respect to the interaction element 9, and in the second position, a relative rotation of the member 1 and the interaction element 9 is prevented.

Moreover, in the first position of the main body 10, the clicker feature 14 or as the case may be the interaction section 13, is displaceable against the resilience of the resilient section 12 (not explicitly indicated in FIGS. 8 and 9). In the second position of the main body 10, the clicker feature 14 interacts with the interaction element 9 such that the clicker feature 14 is not displaceable against the resilience of the resilient section 12 anymore.

In the depicted situation, the member 1 is in the first position with respect to the housing 3. As a further difference to the previously described assembly, the assembly 100 shown in FIG. 5 comprises an interaction element 9 which is arranged distally (underneath) with respect to the member 1. In the second position of the main body 10, the resilient section 12 may be permanently compressed and the clicker mechanism is prevented from being activated or functioning.

In FIG. 9, a portion of the assembly 100 of FIG. 8 is shown from a different angular perspective (after a certain rotation of the assembly 100 around the longitudinal axis Y). It is shown that the interaction element 9 is engaged with the housing 3 via protrusions 6. By means of the protrusion 6, the interaction element 9 can be rotationally locked with respect to the housing 3.

In FIGS. 8 and 9 parts of an assembly 100 are shown respectively. These images may also relate to drug delivery devices in which the assembly is applied.

Figure 10:
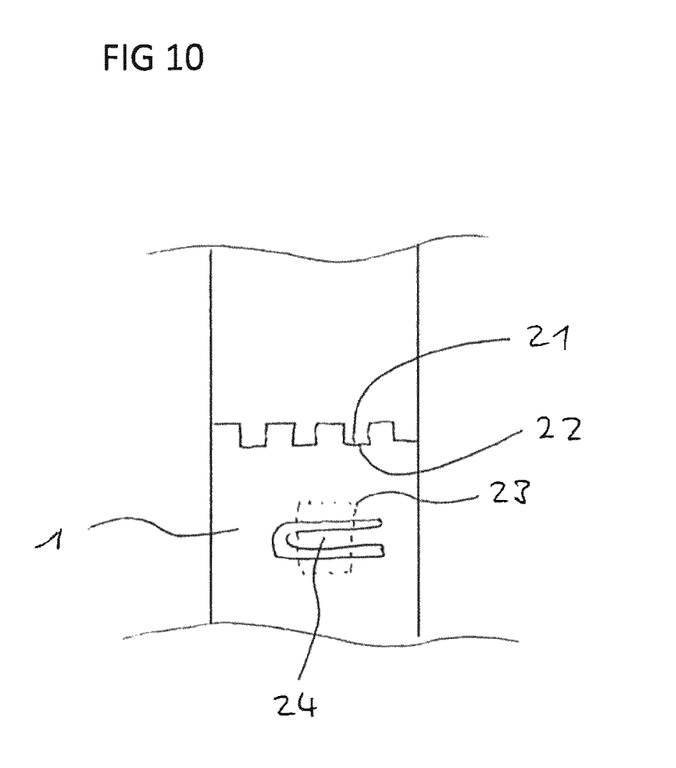
FIG. 10 shows a part of a schematic side view of the member and a further component being in a clutch engagement of with the member.

In FIG. 10, it is shown schematically that the member 1, particularly the main body 10, comprises an additional feature 22 at a proximal end of the member 1. The member 1 is shown in the first position. A further component (not explicitly indicated) of the assembly 100 or the device, such as the above-mentioned dial sleeve comprises the clutch feature 21. The clutch feature 21 and the additional feature 22 are arranged to engage each other in a clutch engagement preventing relative rotational movement of the clutch feature 21 and the additional feature 22. The clutch feature 21 and the additional feature 22 are, preferably, biased into the clutch engagement by way of the resilient section 12. The assembly 100 may further be configured such that in a second position of the main body 10, a clutch mechanism is released.

In addition to the clutch mechanism, the assembly or the drug delivery device may comprise a feedback mechanism which comprises a first feedback feature 23 and a second feedback feature 24 (cf. FIG. 10). The first feedback feature 23 is, preferably, provided by the above-mentioned sleeve or a further component, e.g. of the assembly 100 or the device. The second feedback feature 24 is, preferably, provided by the main body 10. The second feedback feature 24 may be a resilient arm. The feedback mechanism is configured such that a relative rotation of the first and the second feedback feature 23, 24 is converted into a feedback by mechanical cooperation of the first and the second feedback feature 23, 24. The feedback mechanism may be a dispense clicker mechanism, i.e. a clicker mechanism operated during a dispensing operation of drug from the assembly or the drug delivery device, for example. The feedback mechanism may require the mentioned clutch mechanism to be released such that the rotation member which may be provided by the component comprising the above-mentioned clutch feature 21 can rotate with respect to the member 1, thereby causing a clicker feedback, such as an audible and or tactile feedback.

With regard to the functioning principle of the above-mentioned dose setting or dose dispensing mechanism of the device, is referred to the document EP 1603611 B1 which is herein incorporated by reference.

The scope of protection is not limited to the examples given herein above. The invention is embodied in each novel characteristic and each combination of characteristics, which particularly includes every combination of any features which are stated in the claims, even if this feature or this combination of features is not explicitly stated in the claims or in the examples.

REFERENCE NUMERALS

1 Member, clutch member
2 Spring element
3 Housing
4 Drive sleeve
5 Fixation element
6 Cut-out
7 Protrusion
8 Counter clicker
9 Interaction element
10 Main body
11 Guidance pin
12 Resilient section
13 Interaction section
14 Clicker feature
20 Piston rod
21 Clutch feature
22 Additional feature
23 First feedback feature
24 Second feedback feature
100 Assembly
X Distance
Y Longitudinal axis

The invention claimed is:

1. A member for a drug delivery device comprising:
a main body,
an interaction section and
a resilient section located at a distal end of the main body and proximal to the interaction section, the main body being unitarily formed with the resilient section and the interaction section, and the interaction section being formed on a distal end of the resilient section,
wherein the resilient section enables axial deflection of the interaction section towards the main body, and wherein the interaction section comprises a clicker element.

2. The member according to claim 1, wherein the main body comprises an additional element being configured to interact with a clutch member.

3. The member according to claim 1, wherein the member comprises in the resilient section, cut-outs to provide the resilience to the resilient section.

4. The member according to claim 3, comprising two cut-outs which are axially spaced with respect to each other.

5. The member according to claim 3, comprising at least one protrusion protruding into at least one cut-out, the protrusion being arranged to limit the resilient movement of the resilient section.

6. The member for a drug delivery device of claim 1, wherein the housing comprises a cartridge containing a pharmaceutically active compound.

7. An assembly for a drug delivery device comprising:
a housing,
an interaction element,
a member comprising:
a main body,
an interaction section, and
a resilient section located at a distal end of the main body and proximal to the interaction section, the main body being unitarily formed with the resilient section and the interaction section, and the interaction section being formed on a distal end of the resilient section, wherein the resilient section enables axial deflection of the interaction section towards the main body, and
wherein the interaction section comprises a clicker element, and
a clicker mechanism comprising the interaction element and the clicker element, wherein the assembly is configured such that, during an operation of the clicker mechanism, a relative rotation between the member and the interaction element is performed such that the resilient section is elastically deformed and the clicker element interacts with the interaction element to perform a clicker action.

8. The assembly according to claim 7, wherein the assembly is configured such that, the main body is displaceable relative to the clicker element between a first position and a second position being different from the first position, wherein in the first position, the member is rotatable with respect to the interaction element and, in the second position, a relative rotation of the member and the interaction element is prevented.

9. The assembly according to claim 8, being configured such that, in the first position of the main body, the clicker element is displaceable against the resilience of the resilient section and, in the second position of the main body, the clicker element interacts with the interaction element such that the clicker element is not displaceable against the resilience of the resilient section.

10. The assembly according to claim 8, wherein the clicker mechanism is suitable to provide for an audible and/or tactile feedback to a user when the member is rotated with respect to the housing in the first position of the main body.

11. The assembly according to claim 7, wherein the clicker element comprises a toothed surface which extends circumferentially around the member.

12. The assembly of claim 7, wherein the housing comprises a cartridge containing a pharmaceutically active compound.

13. A drug delivery device comprising:
a drive mechanism configured to eject a drug; and
a housing,
an interaction element,
a member comprising:
    a main body,
    an interaction section, and
    a resilient section located at a distal end of the main body and proximal to the interaction section, the main body being unitarily formed with the resilient section and the interaction section, and the interaction section being formed on a distal end of the resilient section, wherein the resilient section enables axial deflection of the interaction section towards the main body, and
wherein the interaction section comprises a clicker element, and
a clicker mechanism comprising the interaction element and the clicker element, wherein the assembly is configured such that, during an operation of the clicker mechanism, a relative rotation between the member and the interaction element is performed such that the resilient section is elastically deformed and the clicker element interacts with the interaction element to perform a clicker action.

14. The drug delivery device according to claim 13, wherein the main body comprises an additional element being configured to interact with a clutch member, and wherein the drug delivery device comprises a clutch mechanism which comprises the clutch member and the additional element which are arranged to engage each other in a clutch engagement, wherein the drug delivery device is configured such that, the clutch member and the additional element are biased into the clutch engagement by the resilient section, and wherein, in the first position of the main body, the clutch engagement is engaged and, in the second position of the main body, the clutch engagement is released.

15. The drug delivery device according to claim 14, comprising, in addition to the clutch mechanism, a feedback mechanism which comprises a first feedback feature and a second feedback feature provided by the main body, wherein the feedback mechanism is configured such that a relative rotation of the first and the second feedback feature is converted into a feedback by mechanical cooperation of the first and the second feedback feature.

16. The drug delivery device of claim 13, wherein the drug comprises a pharmaceutically active compound, and wherein the housing comprises a cartridge containing the drug.

17. A drug delivery device comprising:
a housing
a drive mechanism
a clicker mechanism comprising:
    a main body,
    an interaction section, and
    a resilient section located at a distal end of the main body and proximal to the interaction section, the main body being unitarily formed with the resilient section and the interaction section, and the interaction section being formed on a distal end of the resilient section,
wherein the resilient section enables axial deflection of the interaction section towards the main body, and wherein the interaction section comprises a clicker element.

18. A method comprising:
rotating a main body of a drug delivery device with respect to a housing and an interaction element of the drug delivery device, the main body comprising an interaction section and a resilient section, with the resilient section located at a distal end of the main body and the interaction section being formed on a distal end of the resilient section, wherein the rotating of the main body comprises the interaction section rotating a tooth of a clicker feature of the interaction section over a tooth of a counter clicker of the interaction element such that the resilient section is axially deflected; and
generating feedback to a user of the drug delivery device corresponding to a unit dose of a drug when the tooth of the clicker element passes over the tooth of the counter clicker and the clicker feature interacts with the interaction element to perform a clicker action.

* * * * *